United States Patent [19]

Huvar

[11] 3,961,043
[45] June 1, 1976

[54] DEODORIZED PESTICIDAL ORGANOTHIOPHOSPHORUS COMPOUNDS

[75] Inventor: Arthur J. Huvar, Richmond, Va.

[73] Assignee: Mobil Oil Corporation, New York, N.Y.

[22] Filed: Aug. 12, 1970

[21] Appl. No.: 63,293

[52] U.S. Cl. .................................. 424/76; 424/213; 424/223; 424/225; 424/365
[51] Int. Cl.$^2$............................................. A01N 9/36
[58] Field of Search ........... 260/989, 963; 424/225, 424/318, 76

[56] References Cited
UNITED STATES PATENTS

| | | | |
|---|---|---|---|
| 2,773,860 | 12/1956 | Mosselman | 260/989 X |
| 3,268,393 | 8/1966 | Wilson | 424/365 X |
| 3,309,432 | 3/1967 | English | 260/989 |

FOREIGN PATENTS OR APPLICATIONS

| | | |
|---|---|---|
| 676,776 | 8/1952 | United Kingdom |
| 886,319 | 1/1962 | United Kingdom |

OTHER PUBLICATIONS

Americal Oil Chem. Soc. Journal 47;371–373, (May 1970).
Americal Oil Chem. Soc. Journal 45:461–464, (1967).
Americal Oil Chem. Soc. Journal 35:225–230, (1957).
Chem. Abstracts, 61:4905b, (1964).

*Primary Examiner*—Leonard Schenkman
*Attorney, Agent, or Firm*—Charles A. Huggett; Howard M. Flournoy

[57] ABSTRACT

Deodorization of organothiophosphorus compounds is achieved by mixing said organothiophosphorus compounds with appropriate amounts of linoleic acid and-/or linolenic acid, or drying oils containing linoleic acid and linolenic acid. Said mixtures are useful as pesticidal compositions having an acceptable or pleasant odor.

11 Claims, No Drawings

3,961,043

DEODORIZED PESTICIDAL ORGANOTHIOPHOSPHORUS COMPOUNDS

BACKGROUND OF THE INVENTION

1. Field of the Invention

This invention is directed to the novel compositions comprising normally malodorous organothiophosphorus compounds (e.g., organothiophosphates and organothiophosphites such as S,S-dipropyl O-ethyl phosphorodithioate and S,S-diethyl O-ethyl phosphorodithioite) and linoleic acid, linolenic acid, drying oils containing linoleic acid and linolenic acid (e.g., linseed oil and tung oil) or mixtures of linoleic acid and linolenic acid to deodorize such organothiophosphorus compounds. It is also directed to pesticidal compositions comprising same.

2. Description of the Prior Art

U.S. Pat. No. 3,112,244 discloses a method for controlling nematodes with certain phosphorothioites and phosphorothioates, and U.S. Pat. No. 3,268,393 discloses a method for killing insects with certain phosphorodithioites and phosphorodithioates.

It is well known in the art that certain aldehydes (i.e., U.S. Pat. No. 3,309,432), peroxides (i.e., U.S. Pat. No. 2,879,284), metallic salts or complexes (i.e., British Patent Number 960,013) and compounds containing unsaturated tertiary carbons (i.e., Netherlands Application 6,412,188) may be used for deodorization of certain organothiophosphorus compounds. No reference is known to my knowledge showing use of linoleic acid, linolenic acid, drying oils containing same, or mixtures of linoleic acid and linolenic acid as a means of deodorizing organothiophosphorus compounds.

SUMMARY OF THE INVENTION

The invention provides compositions comprising mixtures of (1) a normally malodorous organothiophosphorus compound of the formula:

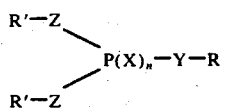

wherein R is a member selected from the group consisting of hydrogen, alkyl (e.g., $C_1$-$C_8$), substituted alkyl (e.g., $C_1$-$C_8$), phenyl, alkyl-substituted phenyl, halo-substituted phenyl, phenyl-substituted phenyl and carbethoxyalkyl, R' is a member selected from the group consisting of alkyl (e.g., $C_1$-$C_8$), X is a member selected from the group consisting of = O and = S, $n$ is the integer 0 or 1, and Y and Z are not the same and are members selected from the group consisting of oxygen and sulfur, and (2) an amount, sufficient to deodorize said organothiophosphorus compound, of a material selected from the group consisting of linoleic acid, linolenic acid, a drying oil and a mixture of linoleic acid and inolenic acid; pesticidal compositions comprising said aforementioned mixtures; and said pesticidal compositions with a carrier therefor.

DESCRIPTION OF SPECIFIC EMBODIMENTS

As will be noted, the compounds for use in the compositions of the present invention are (1) organothiophosphorus compounds which have a characteristic objectionable odor and (2) a deodorizing compound. Non-limiting example of organothiophosphorus compounds which may be used in the mixture compositions of the present invention include compounds having the general structure:

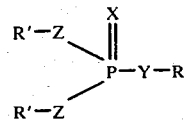

wherein R, R', X, Y and Z are as hereinbefore defined, such as
S,S-dibutyl O-methyl phosphorodithioate,
S,S-dipropyl O-ethyl phosphorodithioate,
S,S-dipropyl O-methyl phosphorodithioate,
S,S-diethyl O-ethyl phosphorodithioate,
S,S-dipropyl O-propyl phosphorodithioate,
S,S-dibutyl O-ethyl phosphorodithioate,
S,S-dimethyl O-ethyl phosphorodithioate,
S,S-dibutyl O-butyl phosphorodithioate,
S,S-dipropyl O-butyl phosphorodithioate,
S-(1,2-dicarbethoxyethyl) O,O-dimethyldithiophosphate,
S-(1,3-dicarbethoxypropyl) O,O-dimethyldithiophosphate, and
S-(1,2-dicarbeth-oxyethyl) O,O-diethyldithiophosphate,
and compounds having the general structure:

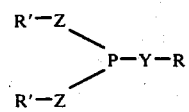

wherein R, R', Y and Z are as hereinbefore defined, such as
S,S-diethyl O-ethyl phosphorodithioite,
S,S-diethyl O-o-tolyl phosphorodithioite,
S,S-diethyl O-m-tolyl phosphorodithioite,
S,S-dipropyl O-propyl phosphorodithioite,
S,S-dibutyl O-ethyl phosphorodithioite,
S,S-diethyl O-methyl phosphorodithioite,
S,S-dipropyl O-methyl phosphorodithioite,
S,S-dipropyl O-ethyl phosphorodithioite,
S,S-dipropyl O-b 2-chloroethyl phosphorodithioite,
S,S-dipropyl O-m-tolyl phosphorodithioite,
S,S-dipropyl O-2,4-dichlorophenyl phosphorodithioite,
S,S-dipropyl O-p-chlorophenyl phosphorodithioite,
S.S-dibutyl O-propyl phosphorodithioite,
S,S-dibutyl O-butyl phosphorodithioite, and
S-propyl S-butyl O-tolyl phosphorodithioite.

Non-limiting examples of deodorizing compounds which may be used in the compositions of the present invention include, in addition to linoleic acid and linolenic acid, and mixtures thereof, drying oils containing one or more of said acids as, in example, linseed oil and tung oil.

In the formulation of the compositions of the present invention, and particularly when the composition is to be used as a pesticide, the liquid deodorizing compound is preferably mixed with the liquid organothiophosphorus compound. When the composition is desired for use as a pesticide, the resulting liquid mix may then be combined with, for example, solid carriers to provide a pesticide in granular form.

The compositions of the present invention may be used in various ways to achieve pesticidal action according to the particular organothiophosphorus compound used. They can be applied as dusts, as liquid sprays, or as gas-propelled sprays, and can contain, in addition to a carrier, additives such as emulsifying agents, wetting agents, binding agents, gases compressed to the liquid state, stabilizers and the like. A wide variety of liquid and solid carriers can be used in the pesticidal compositions. Non-limiting examples of liquid carriers include water; organic solvents, such as alcohols, ketones, amides, and esters; mineral oils, such as kerosene, light oils, and medium oils; and vegetable oils, such as cottonseed oil. Non-limiting examples of solid carriers include talc, bentonite, diatomaceous earth, pyrophyllite, fuller's earth, gypsum, flours derived from cotton seeds and nut shells, and various natural and synthetic clays having a pH not exceeding about 9.5.

In practice, pesticidal compositions may be prepared in the form of concentrates, which are diluted in the field to the concentration desired for application. For example, the concentrate mixture can be a wettable powder containing large amounts of organothiophosphorus compound, a carrier (e.g., attapulgite or other clay), and wetting and dispersing agents. Such powders can be diluted prior to application by dispersing them in water to obtain a sprayable suspension containing the concentration of organothiophosphorus compound desired for application. Other concentrate mixtures can be solutions that can be later diluted, e.g., with kerosene. Thus, it is within the contemplation of this invention to provide pesticidal compositions containing up to about 80 percent, by weight of the composition, of organothiophosphorus compound. Accordingly, depending upon whether it is ready for application or it is in concentrated mixture form, the contemplated pesticidal compositions contain between about 0.0001 percent and 80 percent, by weight of the composition of at least one organothiophosphorus compound derivative and a carrier, liquid or solid, as defined hereinbefore.

The following examples demonstrate typical procedures of formulation of deodorized dry organothiophosphorus compounds.

EXAMPLE 1

One part of boiled linseed oil was mixed with six parts of liquid S,S-dipropyl O-ethyl phosphorodithioate at room temperature. After mixing, a granular product was formulated containing 10% of the organothiophosphorus compound by slowly dripping the liquid mixture onto granular Attaclay (attapulgite clay) of 30–60 mesh with vigorous stirring.

EXAMPLE 2

One part boiled linseed oil was mixed with five parts of liquid S-(1,2-dicarbethoxyethyl) O,O-dimethyldithiophosphate (Malathion) at room temperature. After mixing, a granular product was formulated as in Example 1.

EXAMPLE 3

One part linoleic acid was mixed with five parts of liquid S,S-dipropyl O-ethyl phosphorodithioate at room temperature. After mixing, a granular product was formulated as in Example 1.

EXAMPLE 4

One part linolenic acid was mixed with five parts of liquid S,S-dipropyl O-ethyl phosphorodithioate at room temperature. After mixing, a granular product was formulated as in Example 1.

TABLE

ODOR COMPARISONS
Odor of the Granular Organothiophosphorus Compound

| Example | Without Deodorizing Compound | With Deodorizing Compound |
| --- | --- | --- |
| 1 | characteristically malodorous | substantially devoid of characteristic odor |
| 2 | characteristically malodorous | substantially devoid of characteristic odor |
| 3 | characteristically malodorous | substantially decreased of characteristic odor |
| 4 | characteristically malodorous | substantially decreased of characteristic odor |

Although the amount of the deodorizing material that may be used may be varied over a rather wide range as long as the desired deodorization is effected, satisfactory results are generally obtained by use of the deodorizing material in an amount up to about 40% by weight of the malodorous compound and, more specifically, in an amount of from about 5 to about 30% by weight of the malodorous compound.

The compositions of the examples were subjected to the standard pesticidal tests for which each respective organothiophosphorus compound is known to have activity. The results of such testing showed that the mixing of the organothiophosphorus compound with the deodorizing compound used in the present invention did not adversely affect pesticidal activity and, in some instances, prolonged or increased such activity.

Although the present invention has been described with preferred embodiments, it is to be understood that modifications and variations may be resorted to, without departing from the spirit and scope of this invention, as those skilled in the art will readily understand.

What is claimed is:

1. A pesticidal composition comprising (1) from about 0.0001 to about 80% by weight of a malodorous compound selected from the group consisting of S,S-dipropyl O-ethyl phosphorodithioate and S-(1,2-dicarbethoxyethyl)O,O-dimethyldithiophosphate, (2) an amount sufficient to deodorize said malodorous compound comprising from about 5 to about 40% by weight of the malodorous compound of a material selected from the group consisting of linoleic acid, linolenic acid and linseed oil, and (3) a liquid or solid carrier.

2. The composition of claim 1 wherein said material is linoleic acid.

3. The composition of claim 1 wherein said material is linolenic acid.

4. The composition of claim 1, wherein said material is linseed oil.

5. The composition of claim 1, wherein said malodorous compound is S,S-dipropyl O-ethyl phosphorodithioate.

6. The composition of claim 5, wherein said material is linseed oil.

7. The composition of claim 1 wherein said malodorous compound is S-(1,2-dicarbethoxyethyl)O,O-dimethyldithiophosphate.

8. The composition of claim 1 wherein said material is present in an amount from about 5 to about 30% by weight of the malodorous compound.

9. The composition of claim 8 wherein the malodorous compound is S(1,2-dicarbethoxyethyl) O,O-dimethyldithiophosphate.

10. The composition of claim 8 wherein the malodorous compound is S,S-dipropyl O-ethyl phosphorodithioate.

11. The composition of claim 10 wherein said material is linseed oil.

* * * * *